United States Patent
Pletcher et al.

(10) Patent No.: US 8,979,271 B2
(45) Date of Patent: Mar. 17, 2015

(54) FACILITATION OF TEMPERATURE COMPENSATION FOR CONTACT LENS SENSORS AND TEMPERATURE SENSING

(71) Applicant: Google Inc., Mountain View, CA (US)

(72) Inventors: Nathan Pletcher, Sunnyvale, CA (US); Zenghe Liu, Alameda, CA (US); Brian Otis, Seattle, WA (US)

(73) Assignee: Google Inc., Mountain View, CA (US)

( * ) Notice: Subject to any disclaimer, the term of this patent is extended or adjusted under 35 U.S.C. 154(b) by 119 days.

(21) Appl. No.: 13/626,542

(22) Filed: Sep. 25, 2012

(65) Prior Publication Data
US 2014/0085600 A1    Mar. 27, 2014

(51) Int. Cl.
*G02C 7/00* (2006.01)
*G02C 7/04* (2006.01)

(52) U.S. Cl.
CPC ........................................ *G02C 7/04* (2013.01)
USPC ...................... 351/219; 351/159.02; 600/319

(58) Field of Classification Search
CPC ........................................... G02C 7/04–7/049
USPC ........ 600/309–367; 351/219, 159.02–159.09, 351/159.1–159.19, 159.2–159.29, 351/159.3–159.38
See application file for complete search history.

(56) References Cited

U.S. PATENT DOCUMENTS

| 3,958,560 | A | 5/1976 | March |
| 4,014,321 | A | 3/1977 | March |
| 4,055,378 | A | 10/1977 | Feneberg et al. |
| 4,122,942 | A | 10/1978 | Wolfson |
| 4,136,250 | A | 1/1979 | Mueller et al. |

(Continued)

FOREIGN PATENT DOCUMENTS

| EP | 0369942 | 5/1990 |
| EP | 686372 | 12/1995 |

(Continued)

OTHER PUBLICATIONS

Liao et al. "A 3microwatt Wirelessly Powered CMOS Glucose Sensor for an Active Contact Lens", Feb. 21, 2011, 2011 IEEE International Solid-State Circuits Conference, Session 2, Technologies for Health/ 2.3, pp. 38-40.*

(Continued)

*Primary Examiner* — Ricky Mack
*Assistant Examiner* — Gary O'Neill
(74) *Attorney, Agent, or Firm* — McDonnell Boehnen Hulbert & Berghoff LLP

(57) ABSTRACT

Apparatus, systems and methods employing contact lens sensors are provided. In some aspects, a contact lens includes a substrate and a circuit. The circuit can include: one or more sensors disposed on or within the substrate, that sense a feature associated with a wearer of the contact lens; and a compensation circuit disposed on or within the substrate, coupled to the sensor(s) and that outputs information to adjust an output of the sensor(s). The compensation circuit can include: a temperature component that senses the temperature of the sensor(s); and a communication component that outputs information indicative of the temperature of the sensor (s), and receives information associated with adjusting the output of the sensor(s). In other aspects, a contact lens includes a circuit that senses the body temperature, or ambient temperature outside of the body, of the contact lens wearer. Sensor fusion and/or calibration can be performed based on the information.

8 Claims, 13 Drawing Sheets

(56) References Cited

U.S. PATENT DOCUMENTS

| | | |
|---|---|---|
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint |
| 5,177,165 A | 1/1993 | Valint et al. |
| 5,177,168 A | 1/1993 | Baron |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0049389 A1* | 4/2002 | Abreu .......................... 600/558 |
| 2002/0191670 A1 | 12/2002 | Huang et al. |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0221276 A1 | 10/2005 | Rozakis et al. |
| 2007/0016074 A1 | 1/2007 | Abreu |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0103368 A1 | 4/2010 | Amirparviz et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |
| 2012/0069254 A1 | 3/2012 | Burton |
| 2012/0075168 A1 | 3/2012 | Osterhout et al. |
| 2012/0075574 A1 | 3/2012 | Pugh et al. |

(56) References Cited

U.S. PATENT DOCUMENTS

| | | | |
|---|---|---|---|
| 2012/0078071 | A1 | 3/2012 | Bohm et al. |
| 2012/0088258 | A1 | 4/2012 | Bishop et al. |
| 2012/0092612 | A1 | 4/2012 | Binder |
| 2012/0109296 | A1 | 5/2012 | Fan |
| 2012/0165635 | A1 | 6/2012 | Radhakrishnan et al. |
| 2012/0177576 | A1 | 7/2012 | Hu |
| 2012/0201755 | A1 | 8/2012 | Rozakis et al. |
| 2012/0245444 | A1 | 9/2012 | Otis et al. |
| 2012/0259188 | A1 | 10/2012 | Besling |

FOREIGN PATENT DOCUMENTS

| | | |
|---|---|---|
| EP | 1061874 | 12/2000 |
| EP | 1617757 | 1/2006 |
| EP | 1818008 | 8/2007 |
| EP | 1947501 | 7/2008 |
| EP | 2457122 | 5/2012 |
| WO | 9504609 | 2/1995 |
| WO | 0116641 | 3/2001 |
| WO | 2001034312 | 5/2001 |
| WO | 03065876 | 8/2003 |
| WO | 2004060431 | 7/2004 |
| WO | 2004064629 | 8/2004 |
| WO | 2006015315 | 2/2006 |
| WO | 2009094643 | 7/2009 |
| WO | 2010105728 | 9/2010 |
| WO | 2010133317 | 11/2010 |
| WO | 2011/011344 | 1/2011 |
| WO | 2011034592 | 3/2011 |
| WO | 2011035228 | 3/2011 |
| WO | 2011035262 | 3/2011 |
| WO | 2011083105 | 7/2011 |
| WO | 2011163080 | 12/2011 |
| WO | 2012035429 | 3/2012 |
| WO | 2012037455 | 3/2012 |
| WO | 2012051167 | 4/2012 |
| WO | 2012051223 | 4/2012 |
| WO | 2012052765 | 4/2012 |

OTHER PUBLICATIONS

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-µW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 µA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

International Searching Authority, International Search Report and Written Opinion for PCT/US2013/059763 mailed Dec. 10, 2013, 13 pages.

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'to project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.

Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.

Lingley, et al., "Multipurpose integrated active contact lenses," SPIE, 2009, 2 pages.

Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.

(56) References Cited

OTHER PUBLICATIONS

Liao, et al., "A 3µW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
Unpublished U.S. Appl. No. 13/240,994, Titled "See-Through Display With Infrared Eye-Tracker,", filed Sep. 22, 2011, 38 pages.
Unpublished U.S. Appl. No. 13/209,706, Titled "Optical Display System and Method with Gaze Tracking,", filed Aug. 15, 2011, 30 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
"Alcohol Detection Technologies: Present and Future," American Beverage Institute, 9 pages.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.
Quick, "Color-changing electrochromic lens technology has fashion and military applications," Gizmag, Jul. 12, 2011, http://www.gizmag.com/electrochromic-lens-technology/19191/, Last accessed Apr. 12, 2012, 4 pages.
Chu, "Contact Lenses that Respond to Light," Technology Review, Nov. 10, 2009, http://www.technologyreview.com/printer_friendly_article.aspx?id=23922, Last accessed Apr. 12, 2012, 2 pages.

\* cited by examiner

FACILITATION OF TEMPERATURE COMPENSATION FOR CONTACT LENS SENSORS AND TEMPERATURE SENSING

TECHNICAL FIELD

This disclosure generally relates to temperature compensation for contact lens sensors and/or temperature sensing via contact lenses.

BACKGROUND

Measuring body temperature and/or ambient temperature is a process often fraught with human-induced errors. Furthermore, a sensor on a contact lens may have an undesired temperature dependence that degrades the accuracy of the sensor measurement. For example, as the temperature of the sensor increases, the sensor accuracy can decrease. Accordingly, apparatus, systems and/or methods of temperature compensation and/or temperature sensing are desired.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its purpose is to present some concepts of one or more aspects in a simplified form as a prelude to the more detailed description that is presented later.

In one or more aspects, the disclosed subject matter relates to a contact lens. In some aspects, the contact lens includes: a substrate; and a circuit. The circuit can include: one or more sensors disposed on or within the substrate and that sense a feature associated with a wearer of the contact lens; and a compensation circuit disposed on or within the substrate and coupled to the one or more sensors and that outputs information to the one or more sensors to adjust an output of the one or more sensors. The compensation circuit can include: a temperature component that senses the temperature of the one or more sensors; and a communication component that outputs information indicative of the temperature of the one or more sensors, and receives information associated with adjusting the output of the one or more sensors.

In one or more aspects, the disclosed subject matter relates to a method of compensating output of a contact lens sensor. The method can include: sensing a feature associated with a wearer of the contact lens; determining a temperature of a sensor that senses the feature and provides an output indicative of the sensed feature; transmitting information indicative of the temperature of the sensor; and receiving information to adjust the output indicative of the sensed feature.

In one or more aspects, the disclosed subject matter relates to another method of compensating output of a contact lens sensor. The method can include: sensing a feature associated with a wearer of the contact lens; determining a temperature of a sensor that senses the feature; and determining information to correct an output of the sensor.

In one or more aspects, the disclosed subject matter relates to another contact lens. The contact lens can include: a substrate; and a circuit. The circuit can include: one or more sensors disposed on or within the substrate and that sense a feature associated with a wearer of the contact lens; and a compensation circuit disposed on or within the substrate, coupled to the one or more sensors and that adjusts an output of the one or more sensors. The compensation circuit can include: a temperature component that senses the temperature of the one or more sensors; an evaluation component that determines information to adjust the output of the one or more sensors based, at least, on the temperature of the one or more sensors; and an adjustment component that adjusts the output of the one or more sensors based, at least, on the information to adjust the output of the one or more sensors.

In one or more aspects, the disclosed subject matter relates to a system. The system can include a contact lens including a substrate and a circuit. The circuit can include: a temperature component that senses at least one of a body temperature of a wearer of the contact lens or an ambient temperature outside of a body of a wearer of the contact lens; and a communication component that outputs sensed temperature information to a sensor processing component.

In one or more aspects, the disclosed subject matter can relate to another method. The method can include: sensing, using a contact lens, at least one of a body temperature of a wearer of the contact lens or an ambient temperature outside of a body of a wearer of the contact lens; and outputting sensed temperature information.

Toward the accomplishment of the foregoing and related ends, the one or more aspects include the features hereinafter fully described and particularly pointed out in the claims. The following description and the annexed drawings set forth herein detail certain illustrative aspects of the one or more aspects. These aspects are indicative, however, of but a few of the various ways in which the principles of various aspects can be employed, and the described aspects are intended to include all such aspects and their equivalents.

DETAILED DESCRIPTION

Figure 1:
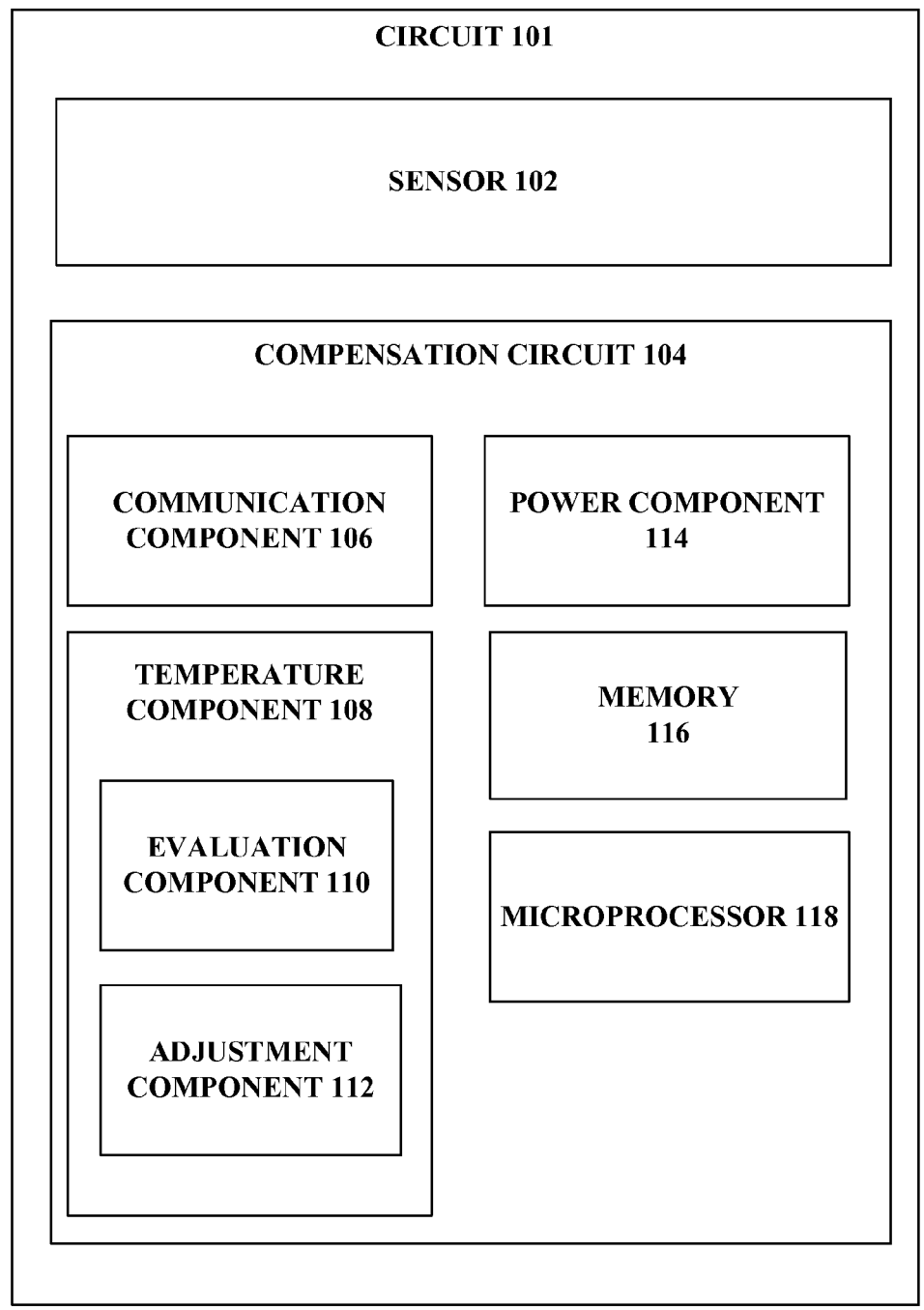
FIG. 1 is an illustration of a block diagram of an exemplary non-limiting system that facilitates temperature compensation for a contact lens sensor in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is be evident, however, that such aspects can be practiced without these specific details. In other instances, structures and devices are shown in block diagram form in order to facilitate describing one or more aspects.

It is to be appreciated that in accordance with one or more aspects described in this disclosure, users can opt-out of providing personal information, demographic information, location information, proprietary information, sensitive information, or the like in connection with data gathering aspects. Moreover, one or more aspects described herein can provide for anonymizing collected, received, or transmitted data.

Apparatus, systems and methods disclosed herein relate to contact lenses performing temperature compensation for sensors on the contact lenses and/or that facilitate body and/or ambient temperature sensing and sensor fusion or calibration. In some aspects, the contact lens includes: a substrate; and a circuit. The circuit can include: one or more sensors disposed on or within the substrate and that sense a feature associated with a wearer of the contact lens; and a compensation circuit disposed on or within the substrate and coupled to the one or more sensors and that outputs information to the one or more sensors to adjust an output of the one or more sensors. The compensation circuit can include: a temperature component that senses the temperature of the one or more sensors; and a communication component that outputs information indicative of the temperature of the one or more sensors, and receives information associated with adjusting the output of the one or more sensors.

In some aspects, the disclosed subject matter relates to another system. The system can include a contact lens including a substrate and a circuit. The circuit can include: a temperature component that senses at least one of a body temperature of a wearer of the contact lens or an ambient temperature outside of a body of a wearer of the contact lens; and a communication component that outputs sensed temperature information to a sensor processing component.

One or more aspects of the apparatus, systems and/or methods described herein can advantageously facilitate contact lens temperature compensation and/or temperature sensing. Accordingly, the aspects can facilitate accuracy of contact lens sensor output while minimizing power consumption and complexity of the contact lens circuitry. In some aspects, on-chip compensation can facilitate analog modulation for sensor reading. In some aspects, the apparatus, systems and/or methods can be employed for sensor fusion and/or calibration of the temperature sensor.

Figure 2:
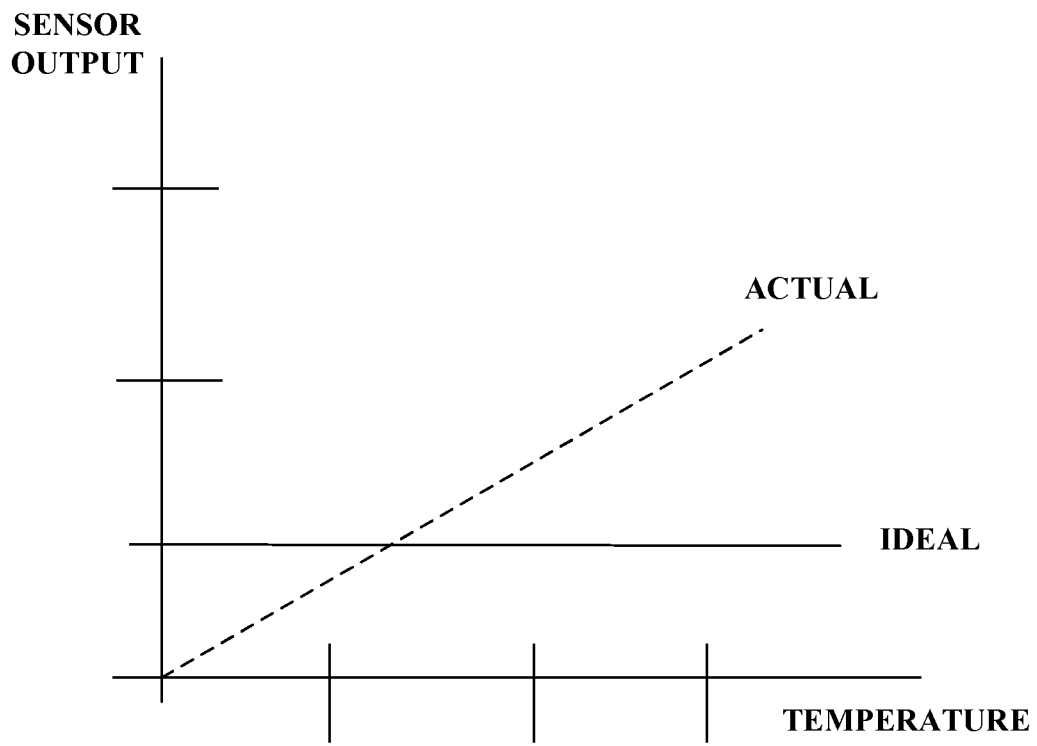
FIG. 2 is an illustration of an exemplary non-limiting graph of sensor output versus temperature for a contact lens sensor in accordance with aspects described herein.
Figure 3:
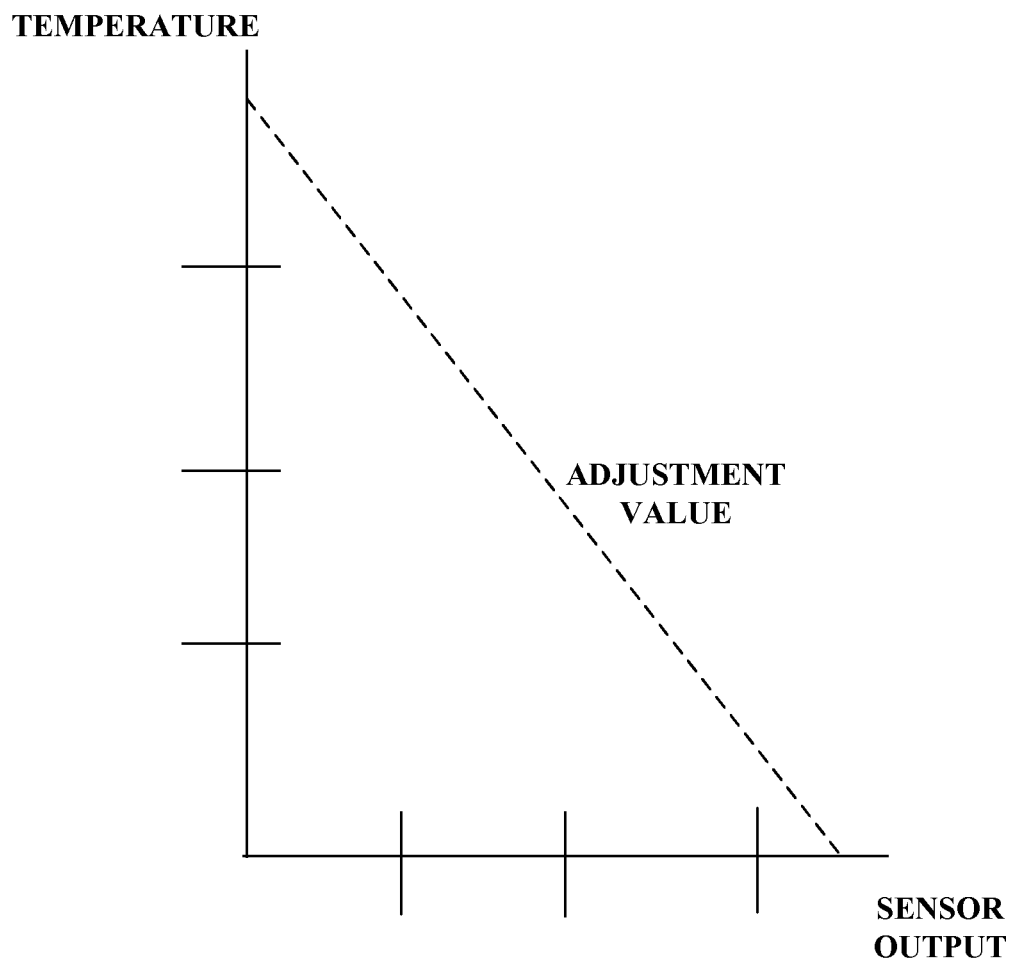
FIG. 3 is an illustration of an exemplary non-limiting graph facilitating temperature compensation for a contact lens sensor in accordance with aspects described herein.

FIG. 1 is an illustration of a block diagram of an exemplary non-limiting system that facilitates temperature compensation for a contact lens sensor in accordance with aspects described herein. The system 100 can be described in greater detail with reference to FIGS. 1, 2 and 3. FIG. 2 is an illustration of an exemplary non-limiting graph of sensor output versus temperature for a contact lens sensor in accordance with aspects described herein. FIG. 3 is an illustration of an exemplary non-limiting graph facilitating temperature compensation for a contact lens sensor in accordance with aspects described herein.

System 100 can be disposed on or within a contact lens in various aspects. In some aspects, system 100 can include a circuit 101 having a sensor 102 and a compensation circuit 104. In various aspects, the sensor 102 and/or compensation circuit 104 can be electrically and/or communicatively coupled to one another to perform one or more functions of the system 100.

In some aspects, the sensor 102 can sense one or more biological features associated with the wearer of the contact lens. The sensor 102 can output a current indicative of a sensed value for the biological feature in various aspects. In some aspects, the sensor 102 can output a value indicative of a level of the sensed biological feature.

In some aspects, the sensed value can vary depending on the temperature of the sensor. As seen in FIG. 2, ideally, the sensor output is independent of the temperature of the sensor. However, in practice, in some aspects, the sensor output can vary in proportion to the temperature of the sensor. Further, while the graph of FIG. 2 shows a linear relationship between current and temperature, in various aspects, the relationship is exponential. For example, a glucose level of a wearer of the contact lens might be constant but the output current of the sensor could increase when the sensor measuring the glucose experiences a temperature increase. Accordingly, the sensor 102 could appear to indicate a sensed increase in glucose level that is actually false.

Accordingly, for a same sensed biological feature value, the actual sensor output can be higher or lower than the true value based on the temperature of the sensor. Because the sensor output can depend on the temperature of the sensor 102, the temperature of the sensor 102 can be employed to calibrate/adjust the output/reading of the sensor 102.

The sensor 102 output/reading can be a current level in some aspects. In some aspects, the sensor 102 output/reading can be a value associated with the biological feature sensed.

The compensation circuit 104 can compensate for the inaccuracy in sensor output based on temperature.

Turning back to FIG. 1, the biological features sensed by the sensor 102 can include, but are not limited to, a glucose level, alcohol level, histamine level, urea level, lactate level and/or cholesterol level of the wearer of the contact lens. In some aspects, the biological feature can include, but is not limited to, a sodium ion ($Na^+$) level, potassium ion ($K^+$) level, calcium ion ($Ca^{2+}$) level or magnesium ion ($Mg^{2+}$) level of the wearer of the contact lens.

The compensation circuit 104 can include a communication component 106, a temperature component 108, an evaluation component 110, an adjustment component 112, a power component 114, a memory 116 and/or a microprocessor 118.

In various aspects, the communication component 106 can transmit and/or receive information indicative of the temperature of the sensor 102, indicative of the information sensed by the sensor (e.g., the biological feature value) and/or indicative of a current output from the sensor 102. In some aspects, the communication component 106 can receive information associated with adjusting the output of the sensor 102. The information can be for correcting the erroneous sensor output that is due to temperature of the sensor 102.

The temperature component 108 can sense the temperature of the sensor 102. In various aspects, the temperature component 108 can adjust the output indicative of the sensed feature based on the information indicative of the temperature of the sensor.

The evaluation component 110 can evaluate the temperature of the sensor 102 and generate information for temperature compensation. For example, in some aspects, the evaluation component 110 can determine an adjustment value that, when subtracted from the current output from the sensor (or, in some aspects, when subtracted from the sensed biological feature value) compensates for the impact the temperature of the sensor 102 has on the current output or feature value. The evaluation component 110 can determine the adjustment value based on the relationship between current and temperature as shown in FIG. 3. While the relationship in FIG. 3 is shown as linear, the graph is merely exemplary, and can be any line having a slope and/or orientation that is generally equal and opposite to that of the actual relationship of the sensor current versus temperature, so as to remove the effects of temperature on the current.

For example, in some aspects, the evaluation component 110 can characterize the output of the sensor 102 as a function of temperature. Specifically, the evaluation component 110 can determine a temperature coefficient that should be associated with the sensor 102. The temperature coefficient can be indicative of a change in current output from the sensor 102 as a function of temperature.

The adjustment component 112 can perform the compensation to the sensor output and generate the adjusted sensor output. For example, employing a graph such as that shown in FIG. 3 (or an algorithm associated with such a graph), in some aspects, the adjustment component 112 can subtract the adjustment value from the output of the sensor (e.g., either the current output and/or the sensed biological feature value) to determine the corrected sensor output. In some aspects, the adjustment component 112 can include information indicative of a slope of sensor output current versus temperature. The adjustment component 112 can also include an adjustment slope having an equal and opposite slope to the sensor output current versus temperature slope. As such, when the sensor increases current output, the adjustment component 112 can subtract a same amount of current to compensate and keep the sensor reading correct.

As another example, in some aspects, the adjustment component 112 can employ the temperature coefficient determined by the evaluation component 110 to determine the proper current for the sensor 102. For example, the adjustment component 112 can multiply the current output from the sensor 102 by the temperature coefficient to generate the corrected current value. The corrected current value can be translated to the corrected sensed biological feature value.

In some aspects, the temperature component 108 can receive the adjustment information from a reader external to the contact lens. For example, the sensor output and/or the temperature sensed can be transmitted to the reader. In various aspects, the reader can include any number of components that can transmit and/or receive information wirelessly including, but not limited to, an RF reader, mobile phone, laptop, personal computer (PC), tablet, personal digital assistant (PDA), head-mounted device or the like. In some aspects, the reader can transmit to the temperature component 108 information for adjustment of the sensed biological feature value. The adjusted biological feature value can then be output from a component of the contact lens. In some aspects, the reader can adjust the sensor output based on the temperature of the sensor and output the adjusted sensor biological feature value.

The power component 114 can generate and/or output power to one or more components of the circuit 101. The power component 114 can provide power to one or more components of the circuit 101 through storing/converting solar energy and/or energy received from radio frequency waves in various aspects.

Figure 4A:
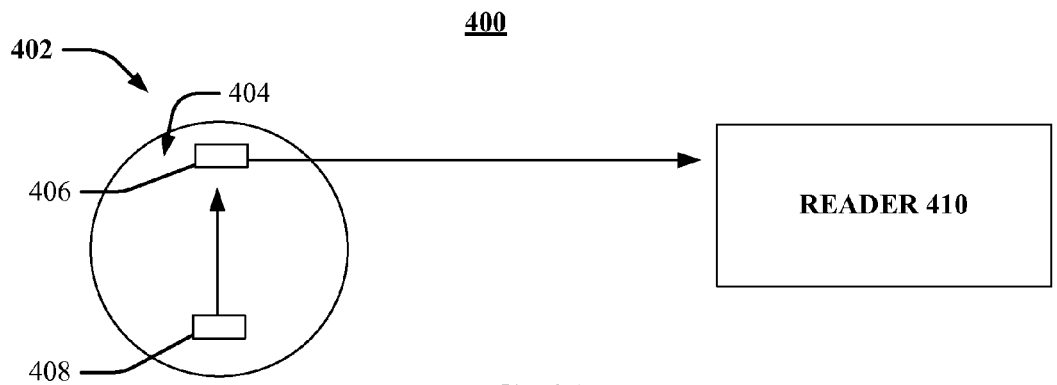
FIGS. 4A, 4B and 4C are illustrations of block diagrams of exemplary non-limiting systems that facilitate temperature compensation for a contact lens sensor in accordance with aspects described herein.
Figure 4B:
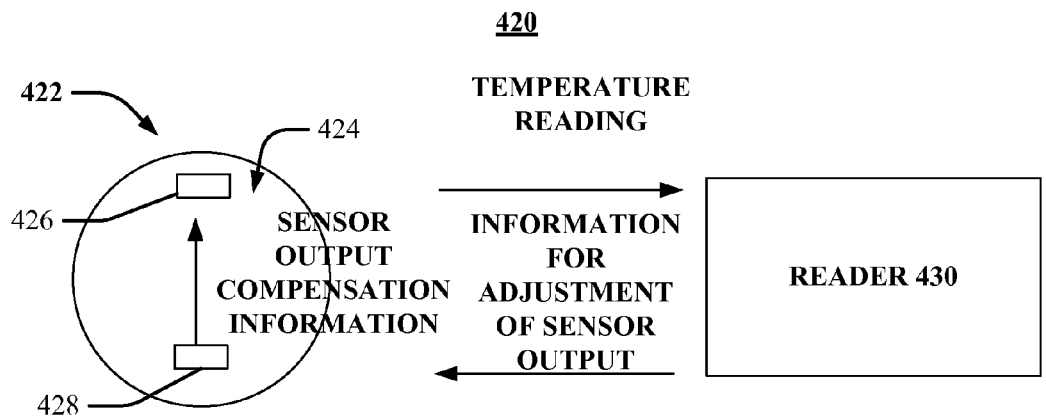
Figure 4C:
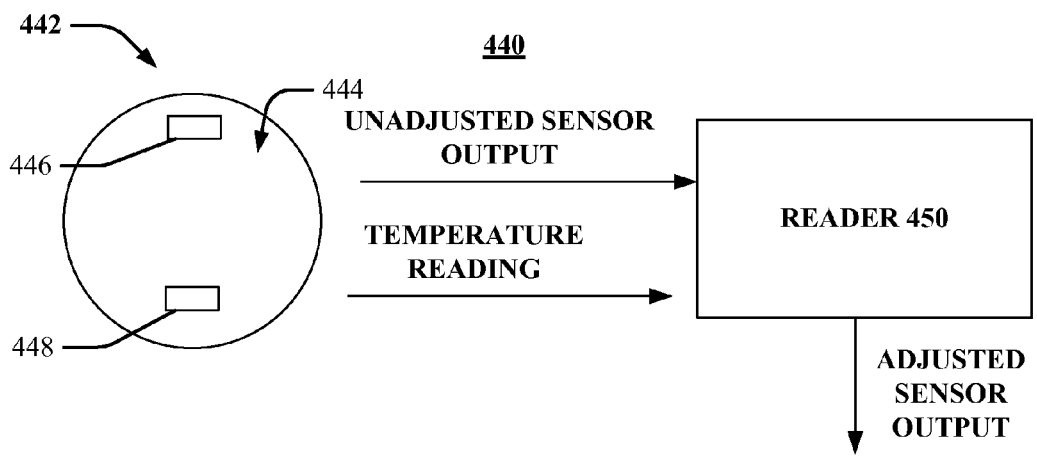

FIGS. 4A, 4B and 4C are illustrations of block diagrams of exemplary non-limiting systems that facilitate temperature compensation for a contact lens sensor in accordance with aspects described herein.

Turning first to FIG. 4A, system 400 can include a contact lens 402 having substrate 404 and a sensor 406 and temperature component 408 on the substrate 404. In some aspects, the system 400 can also include a reader 410. The sensor 406, temperature component 408 and/or reader 410 can be electrically and/or communicatively coupled to one another to perform one or more functions of the contact lens 402 and/or system 400.

The sensor 406 can sense a biological feature of a wearer of a contact lens. The temperature component 408 can perform temperature compensation for the sensor 406. For example, the temperature component 408 can determine the temperature of the sensor 406. Based on the temperature of the sensor 406, the temperature component 408 can determine information for compensating the output from the sensor 406. The adjusted sensor output can be transmitted to the reader 410 as shown. Accordingly, the temperature component 408 can perform correction to the output from the sensor 406 based on the temperature of the sensor 406.

Turning now to FIG. 4B, system 420 can include a contact lens 422 having substrate 424 and a sensor 426 and temperature component 428 on the substrate 424. In some aspects, the system 420 can also include a reader 430. The sensor 426, temperature component 428 and/or reader 430 can be electrically and/or communicatively coupled to one another to perform one or more functions of the contact lens 422 and/or system 420.

The sensor 426 can sense a biological feature of a wearer of a contact lens. The temperature component 428 can perform temperature compensation for the sensor 426. In this aspect, the temperature of the sensor 426 can be output to the reader 430. The reader 430 can perform one or more calculations for adjusting the output of the sensor. The adjustment can be based on the received temperature reading for the sensor 426. The contact lens 422 can receive the information for adjustment of the output of the sensor 426. The temperature component 428 can apply the information to adjust the output of the sensor 426. Accordingly, the temperature component 428 can perform correction to the output from the sensor 426 based on the temperature of the sensor 426 and the compensation information received from the reader 430.

Turning now to FIG. 4C, system 440 can include a contact lens 442 having substrate 444 and a sensor 446 and temperature component 448 on the substrate 444. In some aspects, the system 440 can also include a reader 450. The sensor 446, temperature component 448 and/or reader 450 can be electrically and/or communicatively coupled to one another to perform one or more functions of the contact lens 442 and/or system 440.

The sensor 446 can sense a biological feature of a wearer of a contact lens. The temperature component 448 can perform temperature compensation for the sensor 446. In this aspect, an unadjusted output from the sensor 446 can be output to the reader 450. The temperature of the sensor 446 can also be output to the reader 450. The reader 450 can perform one or more calculations for adjustment of the output of the sensor 446. The adjustment can be based on the received temperature reading for the sensor 446. The reader 450 can adjust the received unadjusted sensor output based on the received sensor temperature information. The adjusted sensor 446 output can be output from the reader 450. Accordingly, the reader 450 can perform correction to the output from the sensor 446 based on the temperature of the sensor 446.

Figure 5:
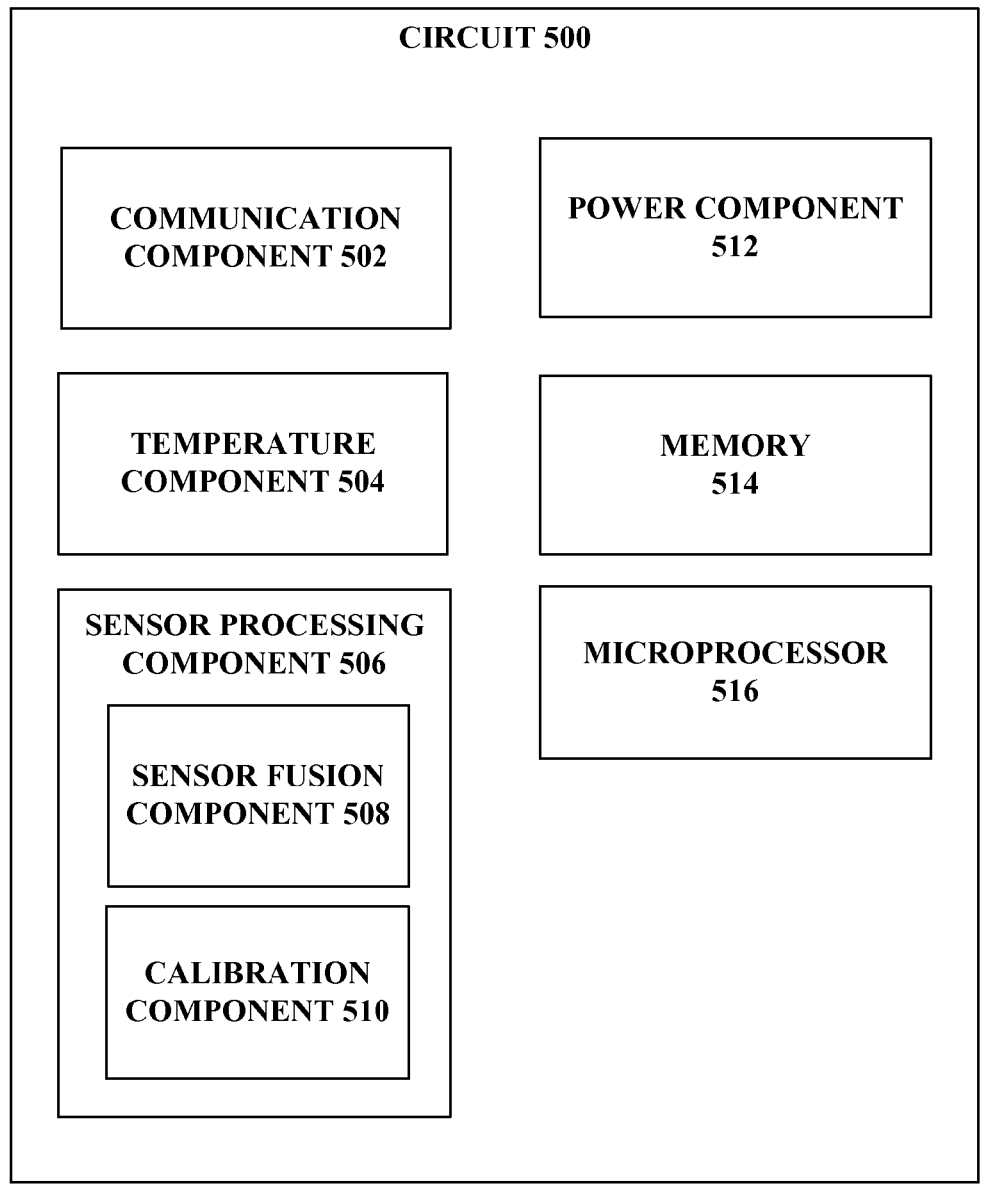
FIG. 5 is an illustration of a block diagram of an exemplary non-limiting circuit that facilitates sensor fusion and/or temperature calibration in accordance with aspects described herein.

FIG. 5 is an illustration of a block diagram of an exemplary non-limiting circuit that facilitates sensor fusion and/or temperature calibration in accordance with aspects described herein. Circuit 500 can include a communication component 502, a temperature component 504, a sensor processing component 506 (which can include a sensor fusion component 508 and/or a calibration component 510), a power component 512, a memory 514 and/or a microprocessor 516. In one or more aspects, the communication component 502, temperature component 504, sensor processing component 506, sensor fusion component 508, calibration component 510, power component 512, memory 514 and/or microprocessor 516 can be electrically and/or communicatively coupled to one another to perform one or more functions of the circuit 500.

The circuit 500 can be disposed on or within a contact lens (not shown) in various aspects. The circuit 500 can be a silicon integrated circuit embedded in the contact lens in various aspects.

The communication component 502 can transmit and/or receive information to and/or from the contact lens. For example, in some aspects, the communication component 502 can transmit temperature information to or from the contact lens. The temperature information can be transmitted and/or received to and/or from a reader external to the contact lens in some aspects.

In one or more aspects, the temperature component 504 can sense a temperature of a body of the wearer of the contact lens and/or of ambient temperature in the environment outside of the body of the wearer of the contact lens.

The sensor processing component 506 can process the temperature information output from the temperature component 504 in various aspects. In some aspects, the sensor processing component 506 can include a sensor fusion component 508 and/or a calibration component 510.

The sensor fusion component 508 can receive the sensed temperature information output from the communication component 502 and/or from the temperature component 504. The sensor fusion component 508 can infer secondary temperature information based on the sensed temperature information. To perform the inferring, the sensor fusion component 508 can use one or more of artificial intelligence approaches and/or hardware or algorithms that can average temperature information from additional sensors and the temperature component 504 on the circuit 500.

In some aspects, the sensor fusion component 508 can infer the secondary temperature information based on additional sensed temperature information output from one or more other sources other than components of the contact lens. For example, when the temperature component 504 measures ambient temperature, additional sensed temperature information can be retrieved from a wearable thermometer, for example.

The calibration component 510 can receive the sensed temperature information output from the communication component 502 and/or the temperature component 504. The calibration component 510 can calibrate the temperature component 504 based on the sensed temperature information output and/or based on additional sensed temperature information output from one or more other sources other than components of the contact lens. For example, the calibration component 510 can calibrate the temperature component 504 based on sensed temperature from other regions of the body other than the contact lens (e.g., when the temperature component 504 senses body temperature via the contact lens) and/or from areas outside of the wearer of the contact lens but proximate to the wearer (e.g., when the temperature component 504 senses ambient temperature via the contact lens).

The power component 512 can generate and/or output power to one or more components of the circuit 500. The power component 512 can provide power to one or more components of the circuit 500 through storing/converting solar energy and/or energy received from radio frequency waves in various aspects.

The memory 514 can be a computer-readable storage medium storing computer-executable instructions and/or information for performing the functions described in this disclosure with reference to the circuit 500. The microprocessor 516 can perform one or more of the functions described in this disclosure with reference to the circuit 500.

Figure 6:
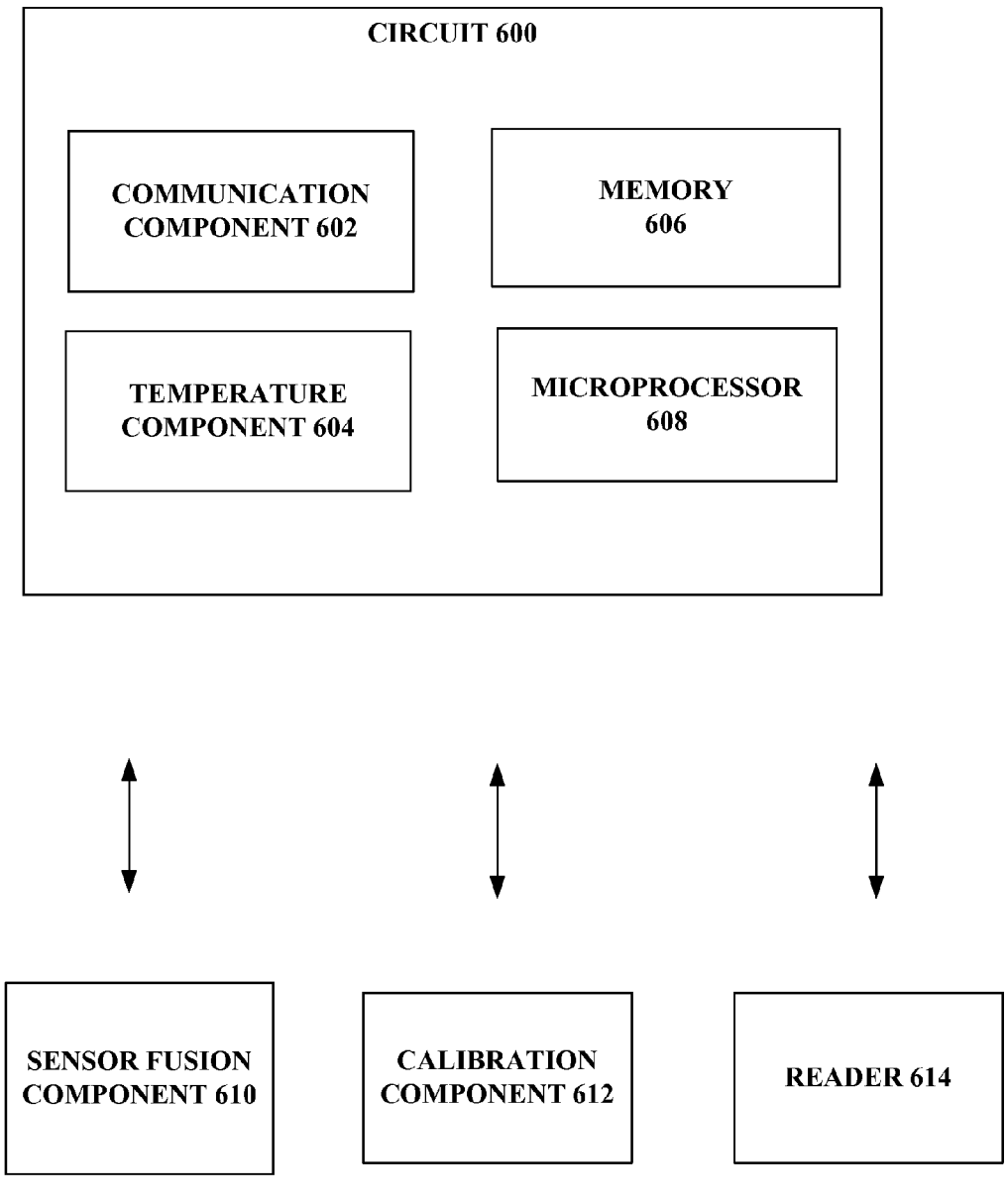
FIG. 6 is an illustration of a block diagram of an exemplary non-limiting circuit that facilitates sensor fusion, temperature calibration and/or temperature sensor reading in accordance with aspects described herein.

FIG. 6 is an illustration of a block diagram of an exemplary non-limiting system that facilitates sensor fusion, temperature calibration and/or temperature sensor reading in accordance with aspects described herein. System 600 can include a communication component 602, a temperature component 604, a memory 606 and/or a microprocessor 608. In one or more aspects, the communication component 602, temperature component 604, memory 606 and/or microprocessor 608 can be electrically and/or communicatively coupled to one another to perform one or more functions of the circuit 600.

The circuit 600 can be disposed on or within a contact lens (not shown) in various aspects. The circuit 600 can be a silicon integrated circuit embedded in the contact lens in various aspects.

The communication component 602 can transmit information from and/or receive information directed to the contact lens. For example, in some aspects, the communication component 602 can transmit temperature information from the contact lens or to one or more other components on the contact lens. The temperature information can be transmitted to and/or received from a sensor fusion component 610, calibration component 612 and/or reader 614 external to the contact lens in some aspects.

In one or more aspects, the temperature component 604 can sense a temperature of a body of the wearer of the contact lens and/or of ambient temperature in the environment outside of the body of the wearer of the contact lens.

The memory 606 can be a computer-readable storage medium storing computer-executable instructions and/or information for performing the functions described in this disclosure with reference to the circuit 600. The microprocessor 608 can perform one or more of the functions described in this disclosure with reference to the circuit 600.

The sensor fusion component 610 can receive the sensed temperature information output from the communication component 602 and/or from the temperature component 604. The sensor fusion component 610 can infer secondary temperature information based on the sensed temperature information. To perform the inferring, the sensor fusion component 610 can use one or more of artificial intelligence approaches and/or algorithms or hardware adapted to average temperature information from additional sensors and the temperature component 604 on the circuit 600.

In some aspects, the sensor fusion component 610 can infer the secondary temperature information based on additional sensed temperature information output from one or more other sources other than the contact lens. For example, when the temperature component 604 measures ambient temperature, additional sensed temperature information can be retrieved from a wearable thermometer, for example.

The calibration component 612 can receive the sensed temperature information output from the communication component 602 and/or the temperature component 604. The calibration component 612 can calibrate the temperature component 504 based on the sensed temperature information output and/or based on additional sensed temperature information output from one or more other sources other than the contact lens. For example, the calibration component 612 can calibrate the temperature component 604 based on sensed temperature from other regions of the body other than the contact lens (e.g., when the temperature component 604 senses body temperature via the contact lens) and/or from areas outside of the wearer of the contact lens but proximate to the wearer (e.g., when the temperature component 604 senses ambient temperature via the contact lens).

The reader 614 can read the information sensed by the temperature component 604 and/or output from the communication component 602 in various aspects.

One or more of the sensor fusion component 610, calibration component 612 and/or reader 614 can include a memory and/or microprocessor for performing one or more functions described in this disclosure.

In aspects wherein the system and/or circuits of FIGS. 1, 5 and/or 6 are employed on the contact lens, in various aspects, only one memory and only one microprocessor need be included on or in communication with the contact lens. In other aspects, more than one memory and/or microprocessor can be included on or in communication with the contact lens.

While not shown, in aspects such as those described with reference to FIGS. 5 and 6, in some aspects, a heat sink can be disposed on or within the contact lens to regulate the temperature of the sensor.

Figure 7:
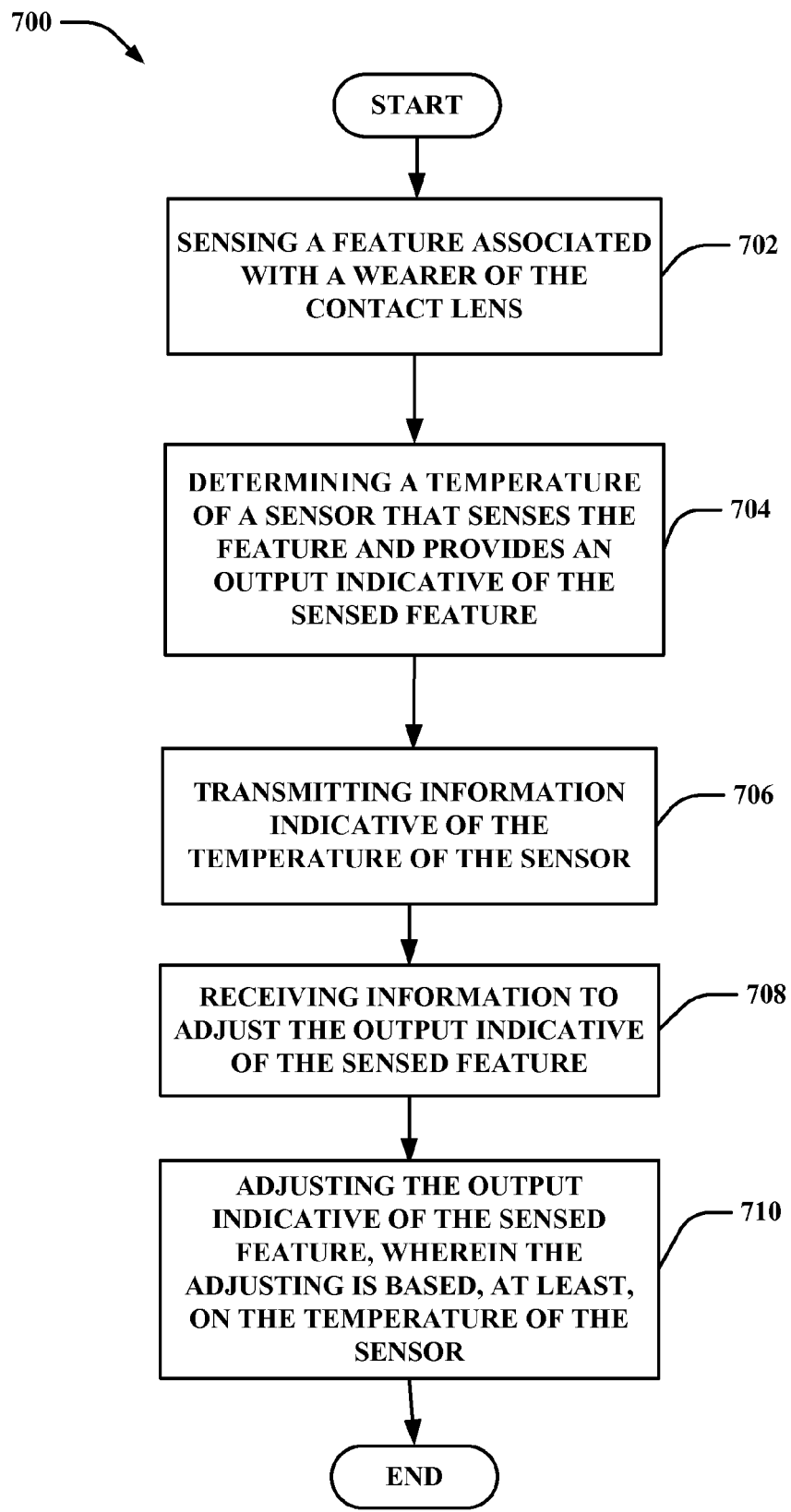
FIGS. 7, 8 and 9 are illustrations of exemplary flow diagrams of methods that facilitate compensation of output of a contact lens sensor in accordance with aspects described herein.
Figure 8:
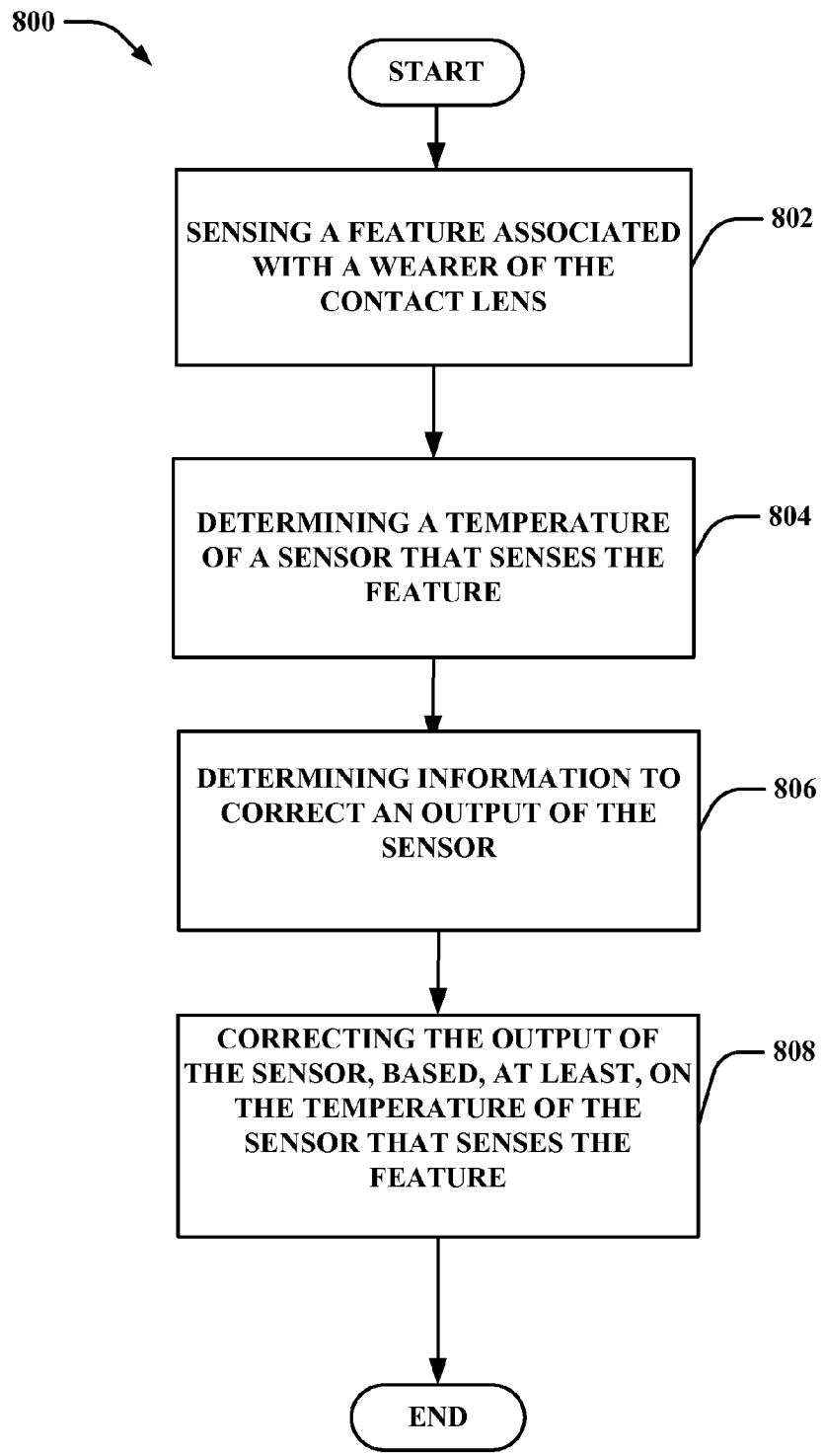
Figure 9:
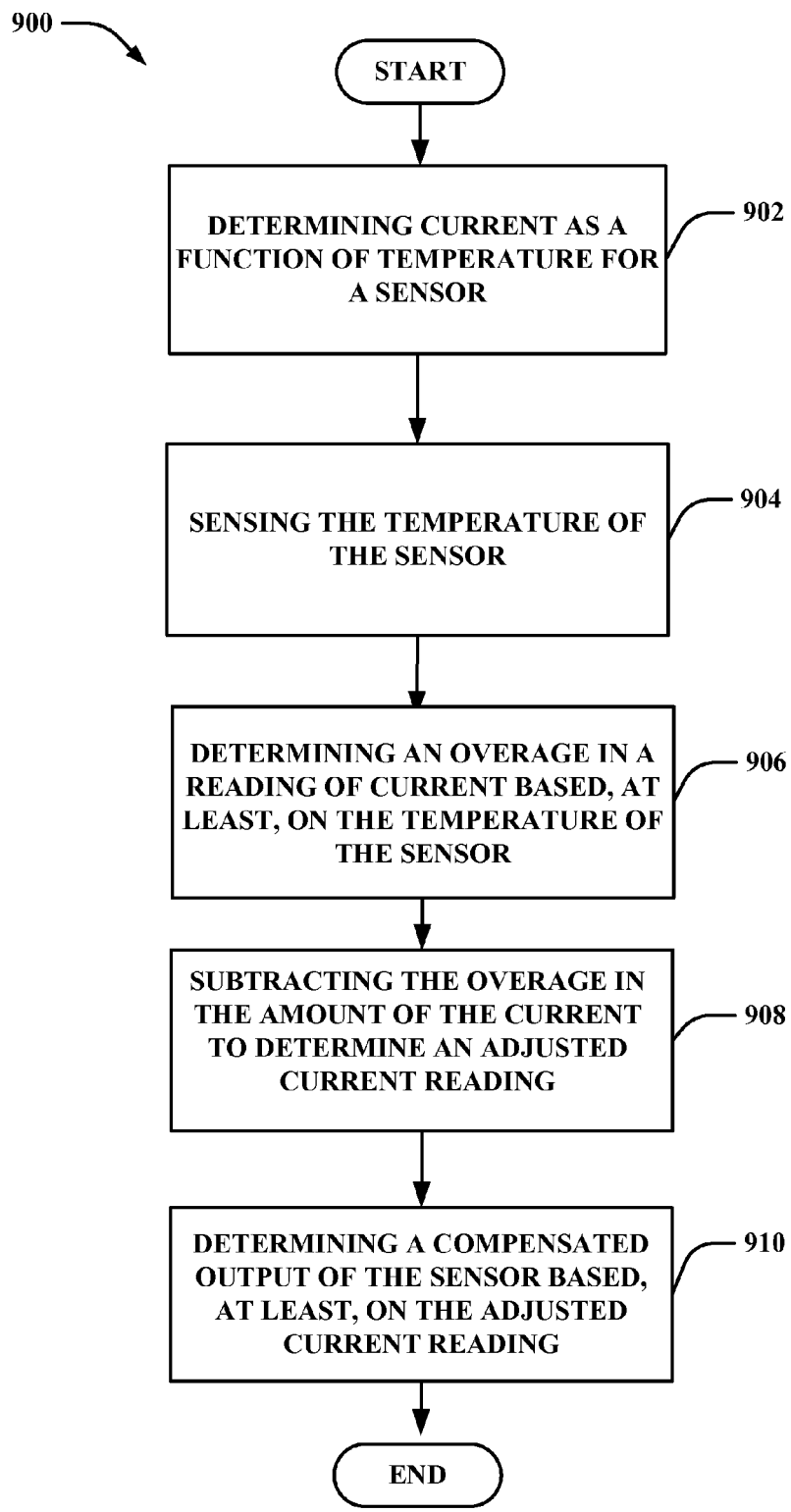

FIGS. 7, 8 and 9 are illustrations of exemplary flow diagrams of methods that facilitate compensation of output of a contact lens sensor in accordance with aspects described herein.

Turning first to FIG. 7, at 702, method 700 can include sensing a feature associated with a wearer of the contact lens (e.g., using the sensor 102). In various aspects the feature sensed can be any number of different types of biological features including, but not limited to, a glucose level, alcohol level, histamine level, urea level, lactate level, cholesterol level, sodium ion ($Na^+$) level, potassium ion ($K^+$) level, calcium ion ($Ca^{2+}$) level or magnesium ion ($Mg^{2+}$) level of the wearer of the contact lens.

At 704, method 700 can include determining a temperature of a sensor that senses the feature and provides an output indicative of the sensed feature (e.g., using the temperature component 108).

At 706, method 700 can include transmitting information indicative of the temperature of the sensor (e.g., using the communication component 106). For example, the information can be transmitted to an external reader that can determine information for compensation or correction/adjustment of the temperature of the sensor. In some aspects, the information determined can be an adjustment value that should be subtracted from the current reading for the sensor and/or from the sensor value. In various aspects, as described in further detail in FIG. 8, for example, the information can be transmitted to a component disposed on or within the contact lens (e.g., evaluation component 110 and/or microprocessor 118) that can determine information for compensation or correction/adjustment of the temperature of the sensor.

At 708, method 700 can include receiving information to adjust the output indicative of the sensed feature (e.g., using the communication component 106). In some aspects, as described in further detail in FIG. 8, for example, the information can be received from the evaluation component 110 and/or microprocessor 118. In some aspects, the information to adjust the output can be calculated based on information stored in the memory 116.

In some aspects, at 710, method 700 can also include adjusting the output indicative of the sensed feature, wherein the adjusting is based, at least, on the information indicative of the temperature of the sensor.

Turning now to FIG. 8, at 802, method 800 can include sensing a feature associated with a wearer of the contact lens (e.g., using the sensor 102). In various aspects the feature sensed can be any number of different types of biological features including, but not limited to, a glucose level, alcohol level, histamine level, urea level, lactate level, cholesterol level, sodium ion ($Na^+$) level, potassium ion ($K^+$) level, calcium ion ($Ca^{2+}$) level or magnesium ion ($Mg^{2+}$) level of the wearer of the contact lens.

At 804, method 800 can include determining a temperature of a sensor that senses the feature (e.g., using the temperature component 108).

At 806, method 800 can include determining information to correct an output of the sensor (e.g., using the evaluation component 110). By way of example, but not limitation, the evaluation component 110 can determine an amount by which to adjust the current reading and/or value output from the sensor. In various aspects, the evaluation component 110 can use, be or be included within the microprocessor 118 that executes instructions stored in memory 116. In some aspects, the evaluation component 110 and/or microprocessor 118 can determine the information to correct the output based on information stored in the memory 116.

In some aspects, at 808, method 800 can include correcting the output of the sensor based, at least, on the temperature of the sensor that senses the feature (e.g., using the adjustment component 112). In various aspects, correcting the output of the sensor can include adjusting the value of the output to compensate for the temperature of the sensor and the corresponding determined inaccuracy in the output resultant from the temperature of the sensor.

Although not shown, in some aspects, method 800 can also include transmitting information indicative of a corrected output of the sensor (e.g., using the communication component 106). In various aspects, the corrected output can be transmitted to a reader external to the contact lens, for example. In various embodiments, the reader can include any number of components that can transmit and/or receive information wirelessly including, but not limited to, an RF reader, mobile phone, laptop, PC, tablet, PDA, head-mounted device or the like.

Turning now to FIG. 9, at 902, method 900 can include determining current as a function of temperature for sensor (e.g., using the temperature component 108). The relationship between the current and the temperature can depend on the type of the sensor. In various aspects, the type of the sensor can be known, and the current-temperature relationship known and/or determined based, at least, on the type of the sensor.

At 904, method 900 can include sensing the temperature of the sensor (e.g., using the temperature component 108).

At 906, method 900 can include determining an overage in a reading of current based, at least, on the temperature of the sensor (e.g., using the evaluation component 110). In some aspects, the overage in the reading of the current can be an excess current reading wherein the excess is due to the temperature of the sensor. The excess can be determined as the overage in the reading of the current.

At 908, method 900 can include subtracting the overage in the amount of the current to determine an adjusted current reading (e.g., using the adjustment component 112). In various aspects, the overage can be subtracted from the current read from the sensor to determine a corrected, or adjusted current reading (and corresponding compensated output of the sensor).

At 910, method 900 can include determining a compensated output of the sensor based, at least, on the adjusted current reading (e.g., using the adjustment component 112).

Figure 10:
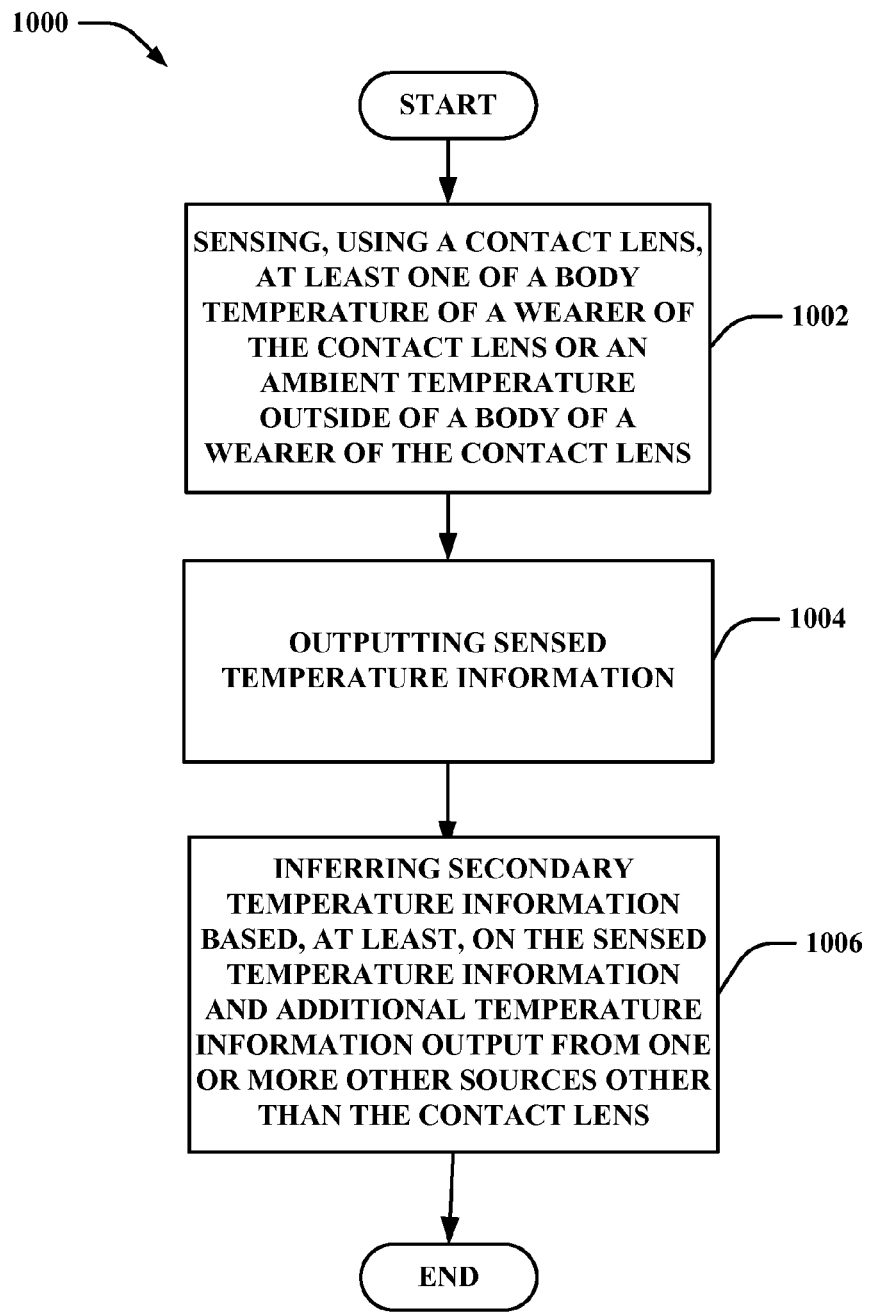
FIGS. 10 and 11 are illustrations of exemplary flow diagrams of methods that facilitate temperature sensing via a contact lens sensor in accordance with aspects described herein.
Figure 11:
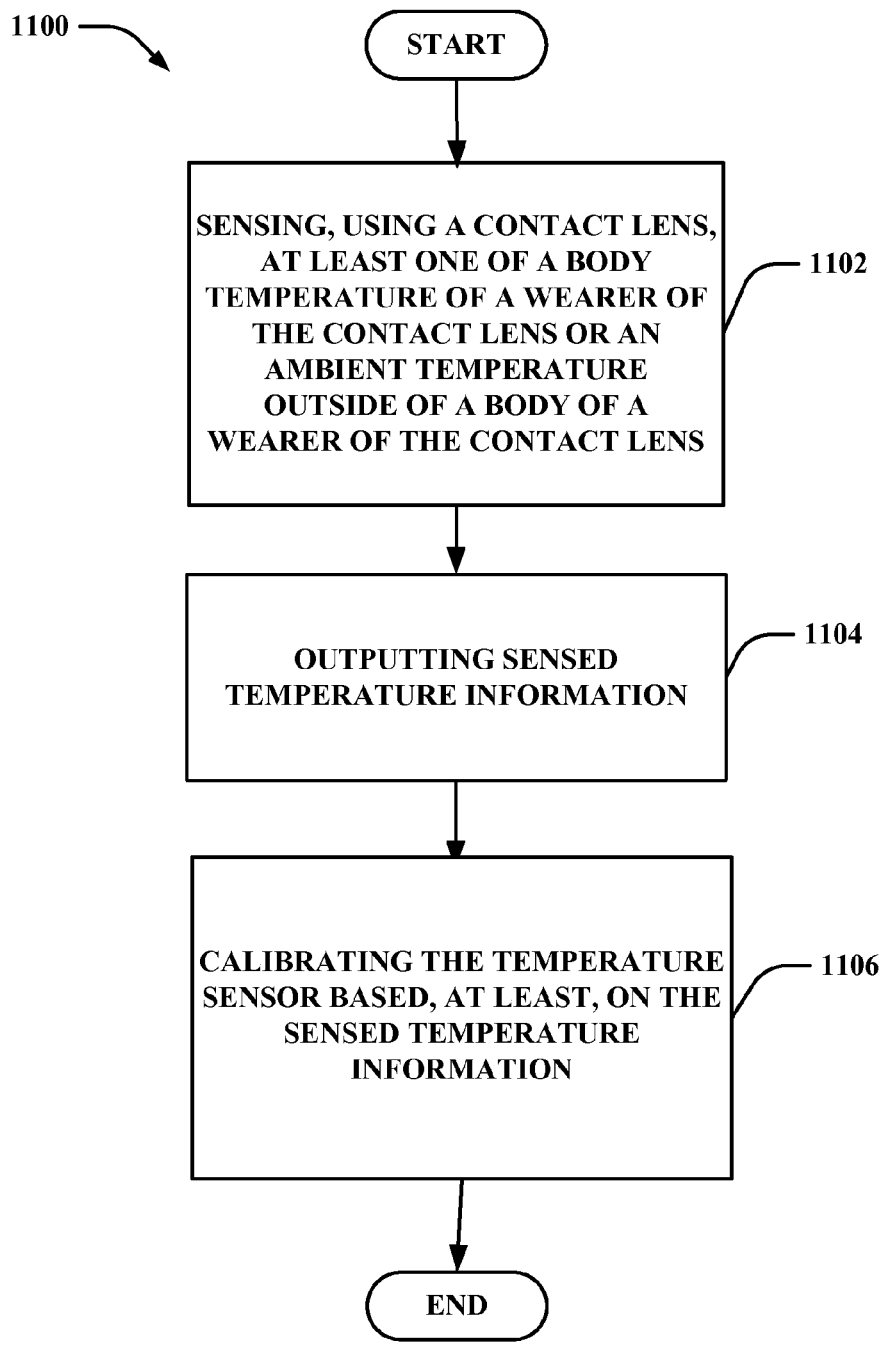

FIGS. 10 and 11 are illustrations of exemplary flow diagrams of methods that facilitate temperature sensing via a contact lens sensor in accordance with aspects described herein.

Turning now to FIG. 10, at 1002, method 1000 can include sensing, using a contact lens, at least one of a body temperature of a wearer of the contact lens or an ambient temperature outside of a body of a wearer of the contact lens (e.g., using the temperature component 504, 604).

At 1004, method 1000 can include outputting sensed temperature information (e.g., using the communication component 502, 602). In various aspects, the information can be output to a reader (e.g., reader 614) and/or another component located remote from the contact lens. In various aspects, the information can be output to another component on the contact lens.

At 1006, method 1000 can include inferring secondary temperature information based, at least, on the sensed temperature information and additional temperature information output from one or more other sources (e.g., using the sensor fusion component 508, 610). For example, in aspects wherein the body temperature is sensed, the additional temperature information can be include, but is not limited to, information from one or more other locations on the body (e.g., from a sensor on a forehead, temple, torso, near the ear canal or the like). In examples in which ambient temperature is sensed, the additional temperature information can include, but is not limited to, information from the environment (e.g., information from sensors located in an area proximate to the area in which the wearer of the contact lens is located, information from a weather service monitoring the area in which the wearer of the contact lens is located, etc.).

Turning now to FIG. 11, at 1102, method 1100 can include sensing, using a contact lens, at least one of a body temperature of a wearer of the contact lens or an ambient temperature outside of a body of a wearer of the contact lens (e.g., using the temperature component 504, 604).

At 1104, method 1100 can include outputting sensed temperature information (e.g., using the communication component 502, 602). In various aspects, the information can be output to a reader (e.g., reader 614) and/or another component located remote from the contact lens. In various aspects, the information can be output to another component on the contact lens.

At 1106, method 1000 can include calibrating the temperature sensor based, at least, on the sensed temperature information (e.g., using the 510, 612). In some aspects, calibrating is further based on additional sensed temperature information output from one or more other sources other than the contact lens. By way of example, but not limitation, the temperature sensor can be calibrated based on the additional sensed temperature reported by a weather service reporting on temperature in an area proximate to the area in which the wearer of the contact lens is located. The temperature sensed on the contact lens can be compared to the temperature reported by the weather service and the temperature component on the contact lens that sensed the temperature can be calibrated based at least in part on the temperature reported by the weather service.

Exemplary Networked and Distributed Environments

One of ordinary skill in the art can appreciate that the various aspects described in this disclosure can be implemented in connection with any computer or other client or server device, which can be deployed as part of a computer network or in a distributed computing environment, and can be connected to any kind of data store. In this regard, the various aspects described in this disclosure can be implemented in association with any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computing devices and systems. These resources and services include the exchange of information, cache storage and disk storage for objects, such as files. These resources and services can also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the various aspects of this disclosure.

Figure 12:
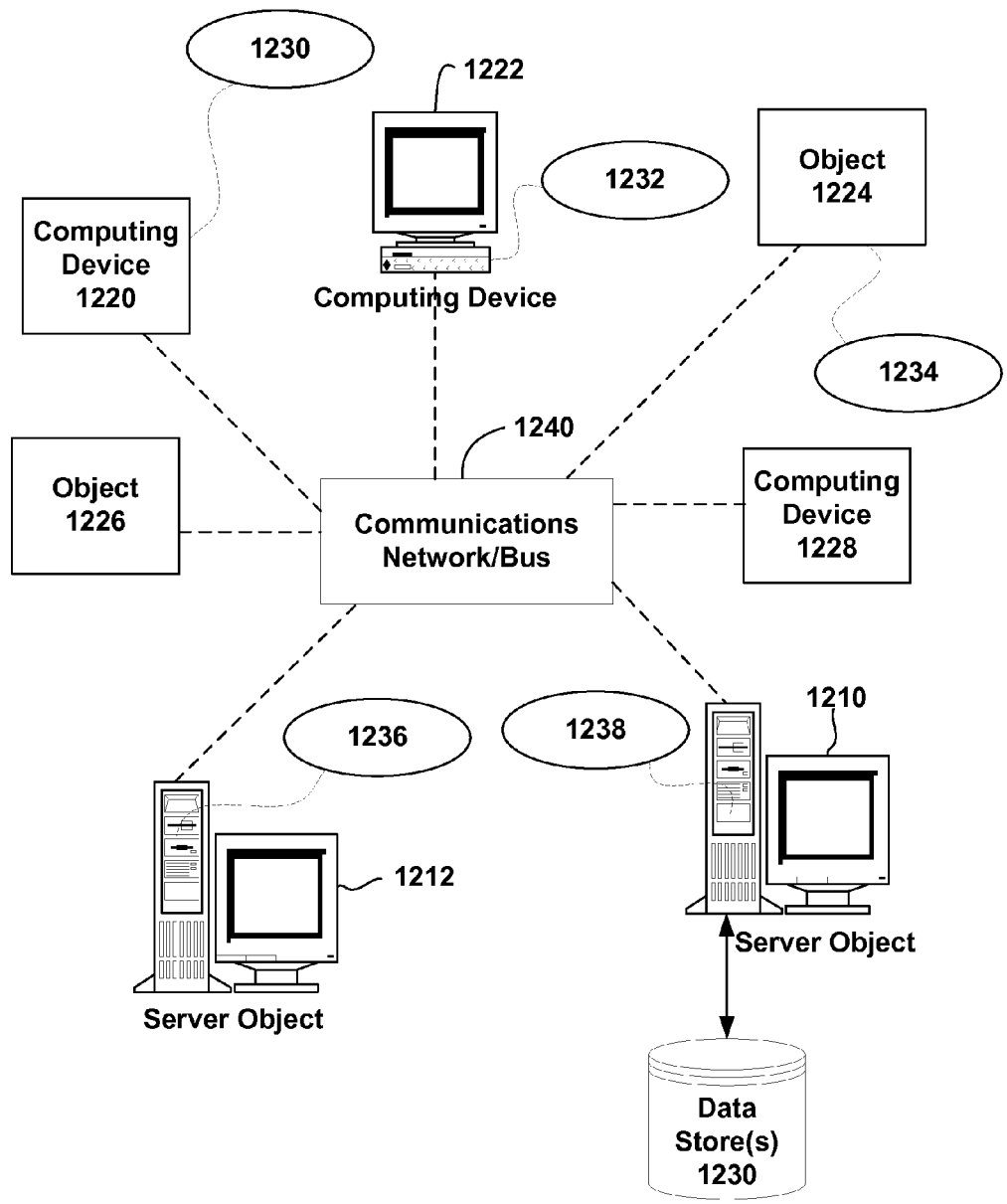
FIG. 12 is an illustration of a schematic diagram of an exemplary networked or distributed computing environment with which one or more aspects described herein can be associated.

FIG. 12 provides a schematic diagram of an exemplary networked or distributed computing environment with which one or more aspects described in this disclosure can be associated. The distributed computing environment includes computing objects 1210, 1212, etc. and computing objects or devices 1220, 1222, 1224, 1226, 1228, etc., which can include programs, methods, data stores, programmable logic, etc., as represented by applications 1230, 1232, 1234, 1236, 1238. It can be appreciated that computing objects 1210, 1212, etc. and computing objects or devices 1220, 1222, 1224, 1226, 1228, etc. can include different devices, such as personal digital assistants (PDAs), audio/video devices, mobile phones, MPEG-1 Audio Layer 3 (MP3) players, personal computers, laptops, tablets, etc.

Each computing object 1210, 1212, etc. and computing objects or devices 1220, 1222, 1224, 1226, 1228, etc. can communicate with one or more other computing objects 1210, 1212, etc. and computing objects or devices 1220, 1222, 1224, 1226, 1228, etc. by way of the communications network 1240, either directly or indirectly. Even though illustrated as a single element in FIG. 12, network 1240 can include other computing objects and computing devices that provide services to the system of FIG. 12, and/or can represent multiple interconnected networks, which are not shown. Each computing object 1210, 1212, etc. or computing objects or devices 1220, 1222, 1224, 1226, 1228, etc. can also contain an application, such as applications 1230, 1232, 1234, 1236, 1238, that might make use of an application programming interface (API), or other object, software, firmware and/or hardware, suitable for communication with or aspect of the various aspects of the subject disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the systems as described in various aspects.

Thus, a host of network topologies and network infrastructures, such as client/server, peer-to-peer, or hybrid architectures, can be utilized. The client can be a member of a class or group that uses the services of another class or group. A client can be a computer process, e.g., roughly a set of instructions or tasks, that requests a service provided by another program or process. A client can utilize the requested service without having to know all working details about the other program or the service itself.

As used in this application, the terms "component," "component," "system," and the like are intended to refer to a computer-related entity, either hardware, software, firmware, a combination of hardware and software, software and/or software in execution. For example, a component can be, but is not limited to being, a process running on a processor, a processor, an object, an executable, a thread of execution, a program, and/or a computer. By way of illustration, both an application running on a computing device and/or the computing device can be a component. One or more components can reside within a process and/or thread of execution and a component can be localized on one computer and/or distributed between two or more computers. In addition, these components can execute from various computer-readable storage media having various data structures stored thereon. The components can communicate by way of local and/or remote processes such as in accordance with a signal having one or more data packets (e.g., data from one component interacting with another component in a local system, distributed system, and/or across a network such as the Internet with other systems by way of the signal).

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

In a client/server architecture, particularly a networked system, a client can be a computer that accesses shared network resources provided by another computer, e.g., a server. In the illustration of FIG. 12, as a non-limiting example, computing objects or devices 1220, 1222, 1224, 1226, 1228, etc. can be thought of as clients and computing objects 1210, 1212, etc. can be thought of as servers where computing objects 1210, 1212, etc. provide data services, such as receiving data from client computing objects or devices 1220, 1222, 1224, 1226, 1228, etc., storing of data, processing of data, transmitting data to client computing objects or devices 1220, 1222, 1224, 1226, 1228, etc., although any computer can be considered a client, a server, or both, depending on the circumstances. Any of these computing devices can process data, or request transaction services or tasks that can implicate the techniques for systems as described in this disclosure for one or more aspects.

A server can be typically a remote computer system accessible over a remote or local network, such as the Internet or wireless network infrastructures. The client process can be active in a first computer system, and the server process can be active in a second computer system, communicating with one another over a communications medium, thus providing distributed functionality and allowing multiple clients to take advantage of the information-gathering capabilities of the server. Any software objects utilized pursuant to the techniques described in this disclosure can be provided standalone, or distributed across multiple computing devices or objects.

In a network environment in which the communications network/bus 1240 can be the Internet, for example, the computing objects 1210, 1212, etc. can be Web servers, file servers, media servers, etc. with which the client computing objects or devices 1220, 1222, 1224, 1226, 1228, etc. communicate via any of a number of known protocols, such as the hypertext transfer protocol (HTTP). Objects 1210, 1212, etc. can also serve as client computing objects or devices 1220, 1222, 1224, 1226, 1228, etc., as can be characteristic of a distributed computing environment.

Exemplary Computing Device

As mentioned, advantageously, the techniques described in this disclosure can be associated with any suitable device. It is to be understood, therefore, that handheld, portable and other computing devices and computing objects of all kinds are contemplated for use in connection with the various aspects, i.e., anywhere that a device may wish to read or write transactions from or to a data store. The data store can read and/or write information to or from a memory (e.g., memory 116, 514, 606), contact lens (e.g., contact lens 402, 422, 442) and/or reader (e.g., reader 410, 430, 450). In various aspects, the data store can be or can include a memory (e.g., memory 116, 514, 606). In some aspects, the data store can be or can include a contact lens (e.g., contact lens 402, 422, 442) as the contact lens can read and/or write transactions to or from one component of the contact lens to another component of the contact lens. In some aspects, the data store can be or can include a reader (e.g., reader 410, 430, 450).

Figure 13:
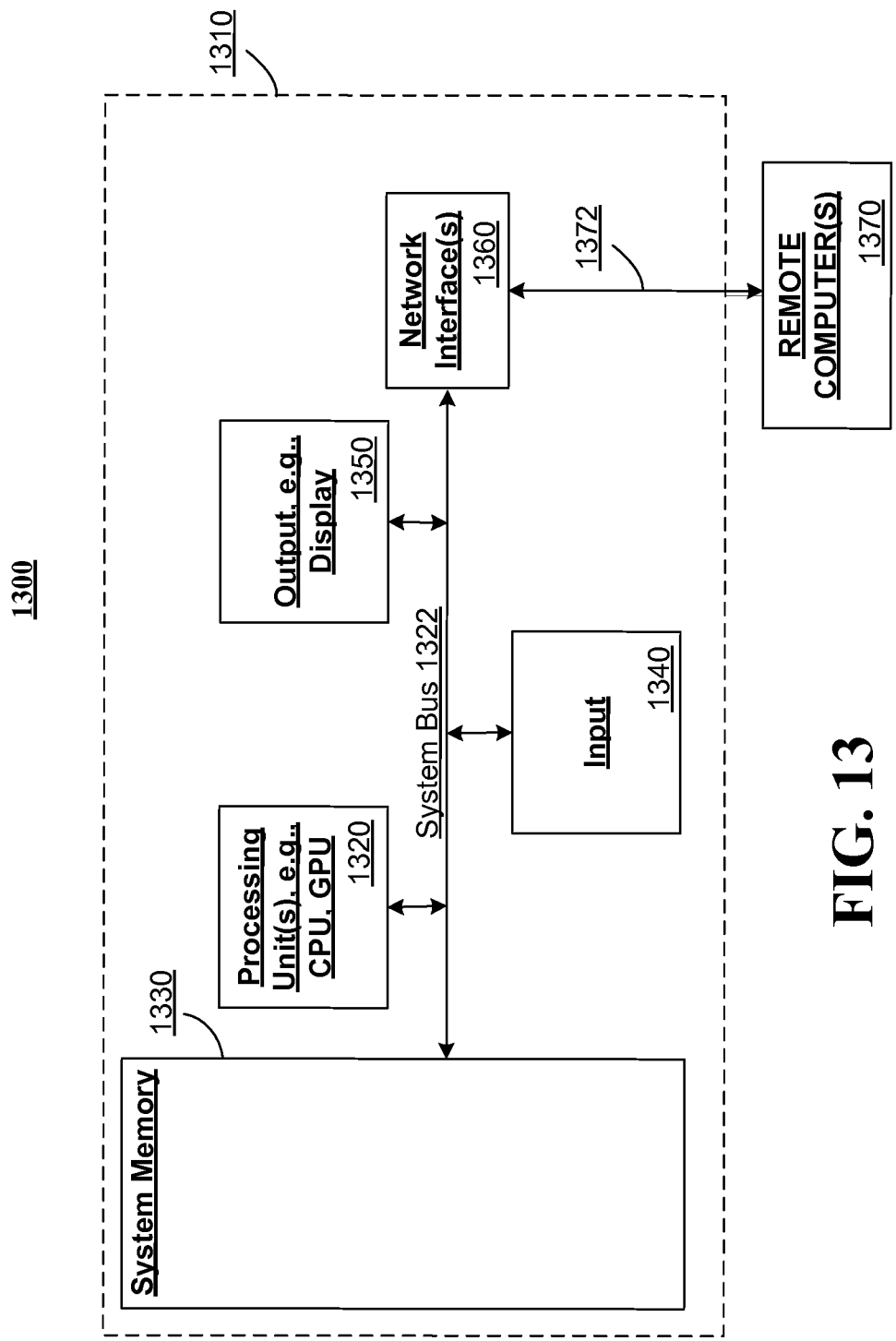
FIG. 13 is an illustration of a schematic diagram of an exemplary computing environment with which one or more aspects described herein can be associated.

Accordingly, the below remote computer described below in FIG. 13 is but one example of a computing device. Additionally, a suitable server can include one or more aspects of the below computer or other server components.

Although not required, aspects can be partly implemented via an operating system, for use by a developer of services for a device or object, and/or included within application software that operates to perform one or more functional aspects of the various aspects described in this disclosure. Software can be described in the general context of computer executable instructions, such as program components, being executed by one or more computers, such as client workstations, servers or other devices. Those skilled in the art will appreciate that computer systems have a variety of configurations and protocols that can be used to communicate data, and thus, no particular configuration or protocol is to be considered limiting.

FIG. 13 thus illustrates an example of a suitable computing system environment 1300 in which one or aspects of the aspects described in this disclosure can be implemented or associated, although as made clear above, the computing system environment 1300 is only one example of a suitable computing environment and is not intended to suggest any limitation as to scope of use or functionality. Neither is the computing environment 1300 to be interpreted as having any dependency or requirement relating to any one or combination of components illustrated in the exemplary computing environment 1300.

With reference to FIG. 13, an exemplary computing environment 1300 for implementing one or more aspects includes a computing device in the form of a computer 1310 is provided. Components of computer 1310 can include, but are not limited to, a processing unit 1320, a system memory 1330, and a system bus 1322 that couples various system components including the system memory to the processing unit 1320.

Computer 1310 typically includes a variety of computer readable media and can be any available media that can be accessed by computer 1310. The system memory 1330 can include computer storage media in the form of volatile and/or nonvolatile memory such as read only memory (ROM) and/or random access memory (RAM). By way of example, and not limitation, memory 1330 can also include an operating system, application programs, other program components, and program data.

A user can enter commands and information into the computer 1310 through input devices 1340, non-limiting examples of which can include a keyboard, keypad, a pointing device, a mouse, stylus, touchpad, touch screen, trackball, motion detector, camera, microphone, joystick, game pad, scanner, video camera or any other device that allows the user to interact with the computer 1310. A monitor or other type of display device can be also connected to the system bus 1322 via an interface, such as output interface 1350. In addition to a monitor, computers can also include other peripheral output devices such as speakers and a printer, which can be connected through output interface 1350.

The computer 1310 can operate in a networked or distributed environment using logical connections to one or more other remote computers, such as remote computer 1380. The remote computer 1380 can be a personal computer, a server, a router, a network PC, a peer device or other common network node, or any other remote media consumption or transmission device, and can include any or all of the elements described above relative to the computer 1310. The logical connections depicted in FIG. 13 include a network 1382, such local area network (LAN) or a wide area network (WAN), but can also include other networks/buses e.g., cellular networks.

Also, there are multiple ways to implement the same or similar functionality, e.g., an appropriate API, tool kit, driver code, operating system, control, standalone or downloadable software object, etc. which enables applications and services to take advantage of the techniques detailed herein. Thus, aspects herein are contemplated from the standpoint of an API (or other software object), as well as from a software or hardware object that implements one or more aspects described in this disclosure. Thus, various aspects described in this disclosure can have aspects that are wholly in hardware, partly in hardware and partly in software, as well as in software.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology or other tangible and/or non-transitory media that can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, radio frequency (RF), infrared and other wireless media.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

When the aspects are implemented in software, firmware, middleware or microcode, program code or code segments, they can be stored in a machine-readable medium (or a computer-readable storage medium), such as a storage component. A code segment can represent a procedure, a function, a subprogram, a program, a routine, a subroutine, a component, a software package, a class, or any combination of instructions, data structures, or program statements. A code segment can be coupled to another code segment or a hardware circuit by passing and/or receiving information, data, arguments, parameters, or memory contents. Information, arguments, parameters, data, etc. can be passed, forwarded, or transmitted using any suitable means including memory sharing, message passing, token passing, network transmission, etc.

For a software aspect, the techniques described in this disclosure can be implemented with components or components (e.g., procedures, functions, and so on) that perform the functions described in this disclosure. The software codes can be stored in memory units and executed by processors. A memory unit can be implemented within the processor or external to the processor, in which case it can be communicatively coupled to the processor via various structures.

The word "exemplary" is used herein to mean serving as an example, instance, or illustration. For the avoidance of doubt, the subject matter disclosed herein is not limited by such examples. In addition, any aspect or design described in this disclosure as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims. Moreover, use of the term "an aspect" or "one aspect" throughout is not intended to mean the same aspect unless specifically described as such. Further, use of the term "plurality" can mean two or more.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is to be noted that one or more components can be combined into a single component providing aggregate functionality or divided into several separate sub-components, and that any one or more middle layers, such as a management layer, can be provided to communicatively couple to such sub-components in order to provide integrated functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks can be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
a substrate; and
a circuit comprising:
a sensor disposed on or within the substrate, wherein the sensor is configured to sense a biological feature and to provide a sensor output indicative of a sensed value of the biological feature, wherein the sensed value is dependent on a temperature of the sensor; and
a compensation circuit disposed on or within the substrate and coupled to the sensor, wherein the compensation circuit comprises:
a temperature component configured to sense the temperature of the sensor;
an adjustment component configured to generate an adjusted sensor output indicative of a corrected value of the biological feature based on the sensor output and on adjustment information, wherein the adjustment information compensates for dependence of the sensed value on the temperature of the sensor; and
a communication component, wherein the communication component is configured to transmit information indicative of the adjusted sensor output to a device external to the contact lens.

2. The contact lens of claim 1, wherein the biological feature is at least one of a glucose level, alcohol level, histamine level, urea level, lactate level or cholesterol level.

3. The contact lens of claim 1, wherein the biological feature is at least one of a sodium ion level, potassium ion level, calcium ion level or magnesium ion level.

4. The contact lens of claim 1, wherein the communication component is further configured to transmit information indicative of the temperature of the sensor to the device external to the contact lens and to receive the adjustment information from the device external to the contact lens.

5. The contact lens of claim 1, wherein the compensation circuit further comprises:
an evaluation component configured to generate the adjustment information based on the temperature of the sensor.

6. A method, comprising:
sensing, by a sensor in a contact lens, a biological feature to provide a sensor output indicative of a sensed value of the biological feature, wherein the sensed value is dependent on a temperature of the sensor;
determining a temperature of the sensor;
transmitting, from the contact lens to a device external to the contact lens, information indicative of the temperature of the sensor;
receiving, at the contact lens from the device external to the contact lens, adjustment information, wherein the adjustment information compensates for dependence of the sensed value on the temperature of the sensor;
generating an adjusted sensor output based on the sensor output and the adjustment information, wherein the adjusted sensor output is indicative of a corrected value of the biological feature; and
transmitting, from the contact lens to a device external to the contact lens, information indicative of the adjusted sensor output.

7. The method of claim 6, wherein the biological feature comprises at least one of a glucose level, alcohol level, histamine level, urea level, lactate level or cholesterol level of the wearer of the contact lens.

8. The method of claim 6, wherein the biological feature comprises at least one of a sodium ion level, potassium ion level, calcium ion level or magnesium ion level of the wearer of the contact lens.

* * * * *